(12) United States Patent
Machida

(10) Patent No.: US 7,008,391 B2
(45) Date of Patent: Mar. 7, 2006

(54) TOOL FOR CORRECTIVE TREATMENT OF INGROWN TOENAIL

(76) Inventor: Eiichi Machida, 1401, Palms Higashinakano, 4-35-2, Kitashinjuku, Shinjuku-ku, Tokyo (JP)

( * ) Notice: Subject to any disclaimer, the term of this patent is extended or adjusted under 35 U.S.C. 154(b) by 84 days.

(21) Appl. No.: 10/838,971

(22) Filed: May 4, 2004

(65) Prior Publication Data
US 2004/0260221 A1 Dec. 23, 2004

(51) Int. Cl.
*A61F 5/11* (2006.01)
(52) U.S. Cl. .......................... 602/30; 602/31
(58) Field of Classification Search ............ 602/30, 602/31
See application file for complete search history.

(56) References Cited

U.S. PATENT DOCUMENTS

| | | | | |
|---|---|---|---|---|
| 1,708,716 A | * | 4/1929 | Andersen | 602/31 |
| 2,024,412 A | * | 12/1935 | Wilson | 602/31 |
| 2,342,530 A | * | 2/1944 | Coates | 602/31 |
| 2,542,324 A | * | 2/1951 | Gibbons | 602/31 |
| 2,613,667 A | * | 10/1952 | Stanley | 602/31 |
| 3,173,416 A | * | 3/1965 | Rederich | 602/31 |
| 4,057,055 A | * | 11/1977 | Clark | 602/31 |
| 4,068,656 A | * | 1/1978 | Barmore | 602/31 |
| 5,012,799 A | * | 5/1991 | Remmen | 602/30 |
| 5,222,643 A | * | 6/1993 | Platt | 224/218 |
| 5,261,872 A | * | 11/1993 | Goldenberg | 602/31 |
| 5,370,140 A | * | 12/1994 | Meyerovich | 132/200 |
| 5,394,890 A | * | 3/1995 | Lambert | 128/846 |
| 5,850,837 A | * | 12/1998 | Shiroyama et al. | 128/892 |
| 6,095,995 A | * | 8/2000 | Machida | 602/30 |
| 2003/0144625 A1 | * | 7/2003 | Sherman et al. | 604/20 |

FOREIGN PATENT DOCUMENTS

JP 2648735 B2 5/1997

* cited by examiner

*Primary Examiner*—Henry Bennett
*Assistant Examiner*—Dinnatia Doster-Greene
(74) *Attorney, Agent, or Firm*—Frishauf, Holtz, Goodman & Chick, P.C.

(57) ABSTRACT

A tool for treatment of an ingrown toenail includes a tubular member having a length of about 1–2 cm and being tapered such that a diameter at a root is about 2 mm and a diameter at a tip is about 2 mm. Holes are distributed over the tubular member. The tubular member has a slit with saw-tooth edges and has a C-shaped cross section. A side edge of a nail plate is inserted into the slit and the saw-tooth edges secure the tubular member to the nail plate. A super elastic wire is inserted into one or more holes to fix the wire to the tubular member. An elastic force of the super elastic wire applied to the side edge of the nail plate is distributed substantially over a whole length of the side edge to correct the side edge into a flat shape.

10 Claims, 5 Drawing Sheets (a)

(b)

(c)

TOOL FOR CORRECTIVE TREATMENT OF INGROWN TOENAIL

BACKGROUND OF THE INVENTION

Field of the Invention

The present invention relates to a tool for corrective treatment of an ingrown toenail with a nail shape correcting member.

An ingrown toenail (Onychocryptosis) occurs when one or both side edges of a toenail plate are bent inwardly into a nail groove or side vallum unguis to compress soft tissues of a toe, which usually accompanies algia or pain. Particularly, an outer side edge Na of a nail plate N of a pollex pedis or big toe F is liable to penetrate a skin as illustrated in FIGS. 6 and 7. The outer side edge Na of the nail plate N compresses soft tissues of the big toe F to cause an infection and sometimes a purulence P might be generated.

FIG. 8(a) shows a condition of an ingrown toenail in which a nail plate N is slightly curved, but side edges of the nail plate do not penetrate the skin. In such a condition, usually any important problem does not occur. However, when side edges Na and Nb of the nail plate N are bent inwardly as depicted in FIG. 8(b) or when the side edges Na and Nb of the nail plate N are inwardly bent to a large extent such that the nail plate N is curved outwardly as illustrated in FIG. 8(c), the nail grooves and side nail vallum unguis are compressed largely. Particularly, when a patient puts on shoes, the big toe F might be compressed and a severe algia might attack the patient.

An ingrown toenail is considered to be caused by congenital factors such as inheritance as well as acquired factors such as compress by shoes and improper nail cutting. In particular, when a nail is cut to the quick, a toe might be infected by bacteria and abnormal granulation might occur and a nail vallum unguis might be inflamed to cause a severe algia.

In order to treat an ingrown toenail, there have been proposed various treating methods. For instance, nail spikes produced at the side edges Na, Nb of nail plate N are cut by a surgical operation. In another method, a cotton packing is inserted between the side edge Na or Nb of nail plate N and soft tissues of a toe. In Japanese Patent No. 2,648,735, there is disclosed a method for corrective treatment of an ingrown toenail with a nail shape correcting member such as a super elastic wire and a super elastic plate made of a shape memory alloy.

When a nail plate N of an ingrown toenail are curved to a large extent and one or both of the side edges of nail plate N penetrate soft tissues of a big toe F, a surgical operation for cutting out nail spikes is rather cumbersome and difficult. There are sometimes occurred another problem that a width of the nail plate N might become narrow and remaining spikes might cause inflammation. Moreover, if there is a fear of infection with bacteria, a surgical treatment could not be performed.

In the method of inserting the cotton packing between the side edges Na, Nb of nail plate N and the soft tissues, since the purulence P produced between the side edges of nail plate and the soft tissues could not be removed effectively, the cotton packing has to be changed frequently.

In the method disclosed in the above mentioned Japanese Patent using a tool for corrective treatment of an ingrown toenail, the tool has to be fastened to the nail plate N. Usually, the corrective treatment tool is formed by a super elastic wire or plate made of a shape memory alloy. In case of using the super electric wire, both ends of the wire are inserted into small holes formed in the nail plate near the distal free edges of nail plate. This corrective treatment is very effective and the nail plate can be flattened. However, when a width of a nail plate N is short, the super elastic wire could not be secured to the nail plate N. Moreover, since the super elastic wire is directly fixed to the nail plate, an elastic force generated by the super elastic wire is locally applied to the nail plate, and therefore the inwardly curved nail plate is not effectively flattened in some cases.

SUMMARY OF THE INVENTION

An object of this invention is to solve the above-mentioned problems and to provide a tool for corrective treatment of an ingrown toenail, by means of which a super elastic wire or plate can be firmly secured to a nail plate to flatten a curved nail plate effectively without causing an inflammation, while a purulence produced between side edges of the nail plate and soft tissues of a toe can be removed effectively.

According to the invention, a tool for corrective treatment of an ingrown toenail with a nail plate shape correcting member comprises:

- a tubular member made of a hard material and having a tapered shape such that a diameter of the tubular member becomes smaller toward a tip;
- a slit formed in said tubular member in a longitudinal direction such that the tubular member has a C-shaped cross sectional configuration; and
- at least one opening formed in said tubular member, said opening having such size and shape that one end of said nail plate shape correcting member is engaged with said opening.

In a preferable embodiment of the tool for corrective treatment of an ingrown toenail according to the invention, said slit is formed to have saw-tooth edges opposed to each other, and a plurality of circular holes are formed in the tubular member such that one end of a super elastic wire made of a shape memory alloy is inserted into one of the holes.

DESCRIPTION OF THE PREFERRED EMBODIMENTS

Now the present invention will be explained in detail with reference to embodiments shown in the accompanying drawings.

Figure 1:
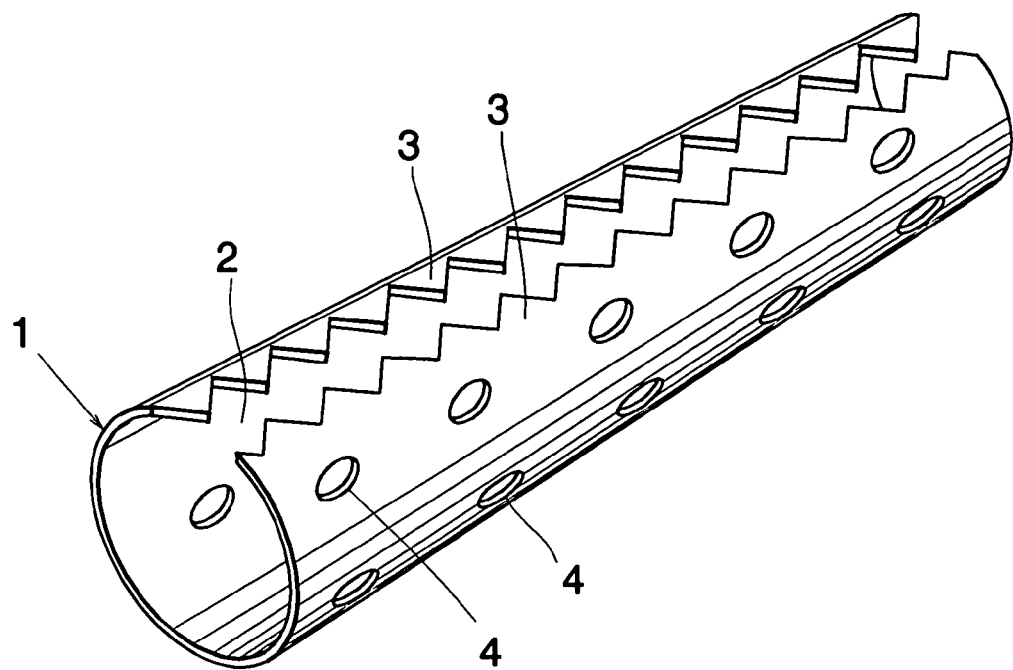
FIG. 1 is a perspective view showing an embodiment of the tool for corrective treatment of an ingrown toenail according to the invention.

FIGS. 1–4 show an embodiment of the tool for corrective treatment of an ingrown toenail according to the present invention. As illustrated in FIG. 1, the tool comprises a tubular member 1 made of a hard material such as titanium alloy and stainless steel alloy and having a length of about 1–2 cm. The tubular member 1 is tapered such that a diameter of the tubular member is gradually decreased from about 4 mm at a root of the tubular member to about 2 mm at a tip. The tubular member 1 has formed therein a slit 2 extending in a longitudinal direction, and thus the tubular member 1 has a C-shaped cross section. In the present embodiment, the slit 2 has a width larger than a thickness of a nail plate N is defined by saw-tooth edges 3 such that a side edge Na of the nail plate N can be easily inserted into the tubular member 1 through the slit 2 and the saw-tooth edges 3 bite on the nail plate N to secure the tubular member 1 to the nail plate stably and effectively. Furthermore, a plurality of circular small holes 4 are formed in the tubular member 1 such that the holes 4 are distributed over the whole surface of the tubular member 1.

Figure 2:
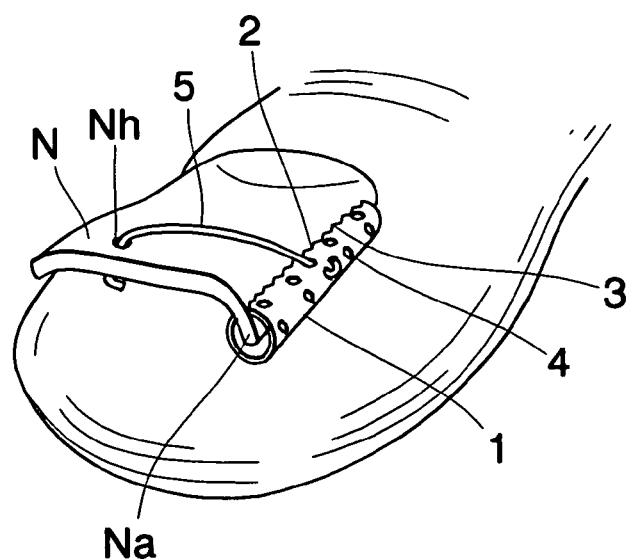
FIG. 2 is a perspective view of the tool which is applied to an actual treatment.
Figure 3:
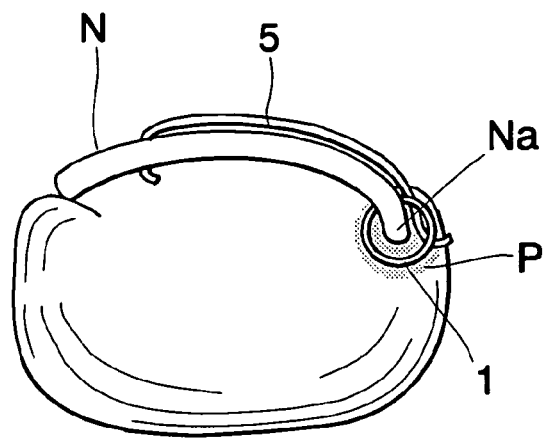
FIG. 3 is a schematic cross sectional view of the tool in use.

FIG. 2 is a perspective view and FIG. 3 is a schematic cross sectional view depicting the tool of corrective treatment under a condition that the tubular member 1 is secured to the nail plate N and a nail shape correcting member is secured to the tubular member 1. In the present embodiment, the nail shape correcting member is formed by a super elastic wire 5 made of a shape memory alloy. Tissues around a side edge Na of the nail plate N is cut with a surgical knife to expose the side edge Na of nail plate N. Then, the tubular member 1 is inserted into the exposed side edge Na through the slit 2, while the tip of the tubular member 1 having the smallest diameter is directed outwardly. After that, the tubular member 1 is compressed with a pincher to reduce a width of the slit 2 such that the saw-tooth edges 3 defining the slit 2 bite on the nail plate N. In this manner, the tubular member 1 can be secured stably and firmly to the nail plate N such that the tubular member 1 surrounds the side edge Na of nail plate N.

After securing the tubular member 1 in the manner explained above, a super elastic wire 5 made of a shape memory alloy and having a suitable diameter selected in accordance with thickness and hardness of the nail is inserted into a suitable hole 4 and one end of the super elastic wire 5 is fixed to the tubular member 1. The other end of the super elastic wire 5 is inserted into a small hole Nh formed in the nail plate N at an untrimmed portion of a grown nail with a needle and is fixed to the nail plate N. A remaining wire is cut off with a nipper. In this manner, one end of the super elastic wire 5 is secured to the side edge Na of nail plate N by means of the tubular member 1 and the other end of the super elastic wire 5 is directly secured to the nail plate N. Due to a strong elasticity of the super elastic wire 5, a force is applied via the tubular member 1 to the side edge Na of nail plate N to move the side edge upward. In this case, the force for moving the side edge Na of nail plate N is applied to the side edge by means of the tubular member 1 which is engaged with the side edge Na of nail plate N over a substantially whole length and the force is not concentrated locally. Therefore, the function of the super elastic wire 5 can be improved to a large extent.

Moreover, soft tissues near the side edge Na of nail plate N are liable to be stimulated by nail spikes and a purulence P is liable to be generated. However, when the tubular member 1 is used, the purulence P can be easily removed through the slit 2 and holes 4 formed in the tubular member 1. In this manner, a possible inflammation can be reduced.

The super elastic wire 5 can continuously apply a force for moving the side edge Na of nail plate N upward as long as the super elastic wire 5 is secured to the nail plate N, the downwardly curved nail plate N can be corrected into a flat shape. Furthermore, a tensional force can be changed by exchanging the super elastic wire 5. For instance, when the nail plate N is flattened to some extent, the super elastic wire 5 is exchanged by another super elastic wire having a smaller diameter. In the present embodiment, since a plurality of holes 4 are formed over a whole surface of the tubular member 1, a position at which the super elastic wire is fixed to the tubular member can be easily changed.

Figure 4:
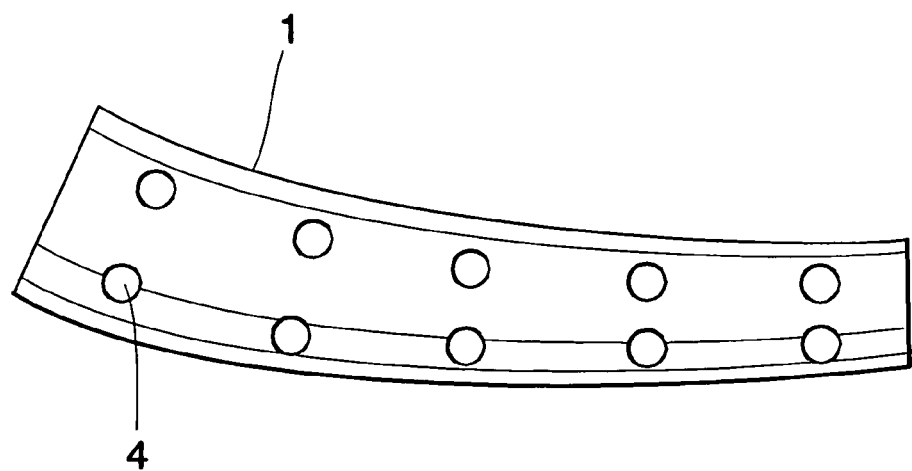
FIG. 4 is a schematic view representing a condition in which the tool is bent.

Upon fixing the tubular member 1 to the side edge Na of nail plate N, the tubular member 1 may be bent as shown in FIG. 4 such that the shape of the tubular member 1 becomes fit to the shape of the side edge Na of nail plate N.

In the present embodiment, the tubular member 1 is made of a metal such as titanium alloy and stainless steel alloy, but according to the invention, the tubular member 1 may be made of another metal alloy or a hard synthetic resin.

Furthermore, in the present embodiment, the tubular member 1 is fitted on the side edge Na of nail plate N, but when both side edges of nail plate are curved downward and penetrate the skin, both side edges may be covered with two tubular members. In this case, both ends of a super elastic wire may be secured to respective tubular members, and therefore it is no more necessary to form a hole Nh in the nail plate N.

In the manner explained above, the present invention can provide the novel and useful tool for corrective treatment of an ingrown toenail, which can be easily, safely and firmly secured to a side edge of nail plate. Moreover, a nail shape correcting member such as a super elastic wire can be easily and firmly secured to the tubular member of the tool. In this manner, the corrective treatment of an ingrown toenail can be easily and effectively conducted and a treatment time can be reduced.

Furthermore, the purulence can be effectively removed through the slit 2 and holes 4 formed in the tubular member 1, and a medicine may be injected through these slit and openings. In this manner, a most effective treatment can be conducted without removing the tool from the nail plate, and therefore a treatment time can be shortened.

Figure 5A:
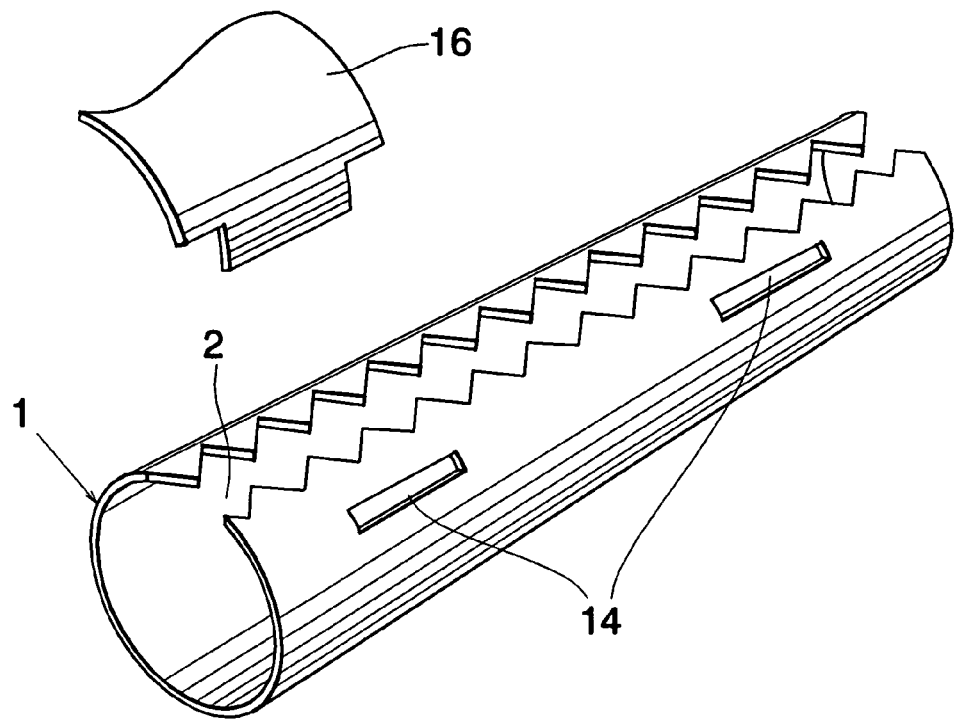
FIGS. 5(a) and 5(b) are perspective views showing another embodiments of the tool for corrective treatment of an ingrown toenail according to the invention.
Figure 5B:
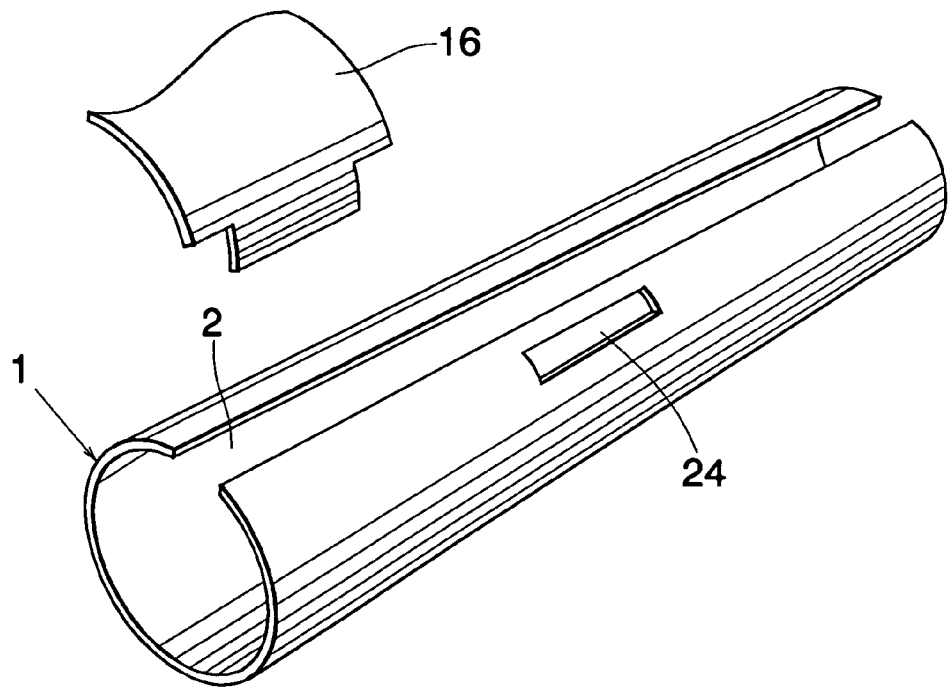
Figure 6:
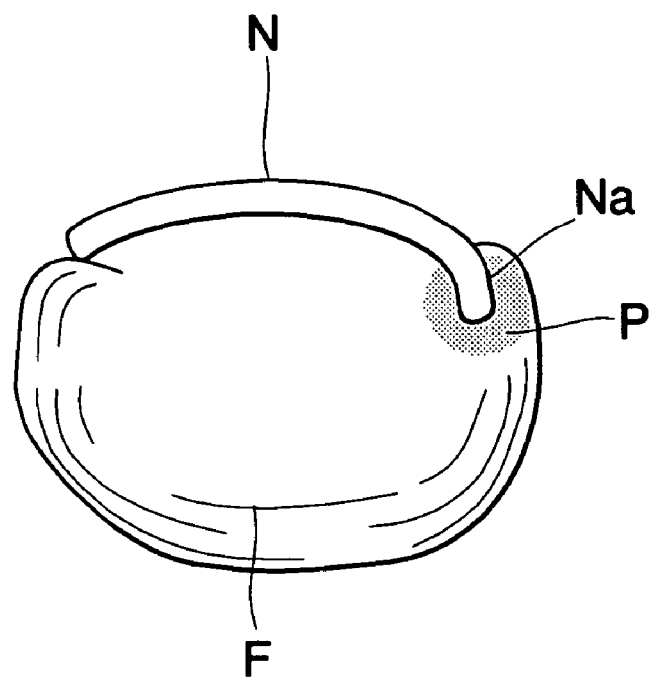
FIG. 6 is a schematic view explaining an ingrown toenail.
Figure 7:
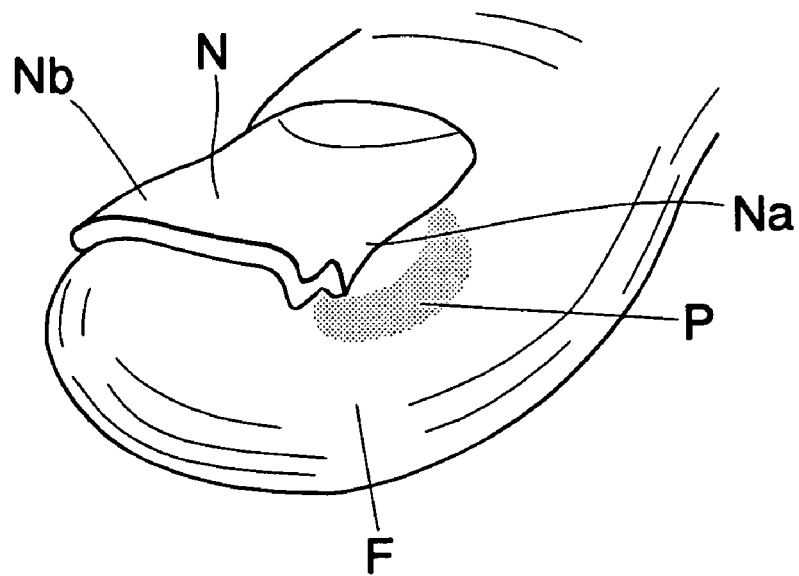
FIG. 7 is a perspective view illustrating the ingrown toenail.
Figure 8:
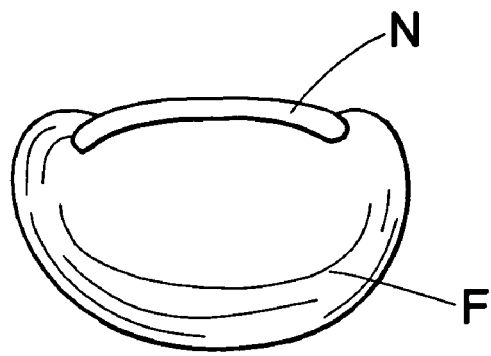
FIGS. 8(a), 8(b) and 8(c) are schematic cross sectional views showing different degrees of the ingrown toenail.
Figure 8:
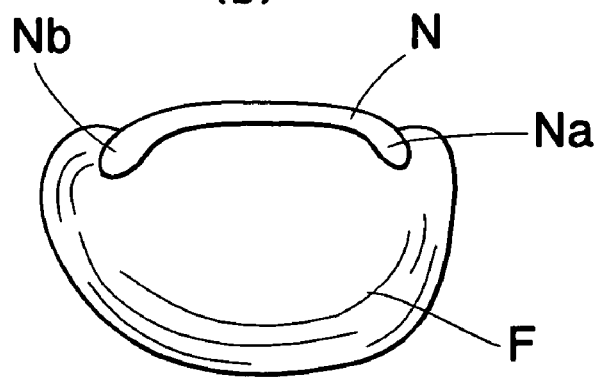
Figure 8:
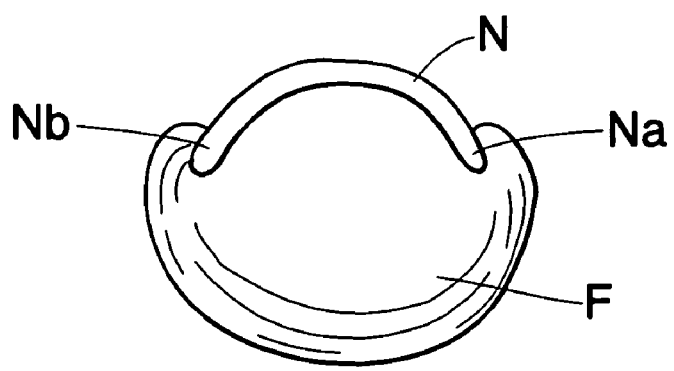

The present embodiment is not limited to the embodiment explained above, but various modifications and alternations may be conceived by a person skilled in the art without departing the scope of the invention. For instance, in the above embodiment, the slit 2 of the tubular member 1 is defined by the saw-tooth edges 3, but the slit may be formed by straight edges. Furthermore, in the above embodiment, a plurality of circular holes 4 are formed in the tubular member 1, but according to the invention, elliptical, rectangular or triangular holes may be formed. For instance, as illustrated in FIG. 5(a), rectangular openings 14 may be formed in the tubular member 1 and a projection 16 formed at the end of a super elastic plate 15 may be inserted into a selected one of the rectangular openings 14. Moreover, as depicted in FIG. 5(b), a opening 17 may be formed at a middle of an edge 2 of a tubular member 1 and the projection 16 of the super elastic plate 15 may be inserted into the opening 17. It should be noted that in the embodiments shown in FIGS. 1 and 5(*a*), it is not always necessary to provide a plurality of openings 4 and 14, but the tubular member may has a single opening. Furthermore, in the embodiment illustrated in FIG. 5(*b*), more than one opening 17 may be formed in the edge 2 defining the slit 2.

What is claimed is :

1. A tool for corrective treatment of an ingrown toenail with a nail plate shape correcting member comprising:
   - a tubular member made of a hard material and having a tapered shape such that a diameter of the tubular member becomes smaller toward a tip;
   - a slit formed in said tubular member in a longitudinal direction such that the tubular member has a C-shaped cross sectional configuration; and
   - at least one opening formed in said tubular member, said opening having such size and shape that one end of said nail plate shape correcting member is engaged with said opening.

2. The tool according to claim 1, wherein a plurality of holes are formed in the tubular member such that the holes are distributed over a whole surface of the tubular member.

3. The tool according to claim 2, wherein each of said plurality of holes has shape and size that an end of said nail plate shape correcting member in a form of a super elastic wire is passed through a hole.

4. The tool according to claim 1, wherein said opening has a rectangular shape such that a projection formed at an end of said nail plate shape correcting member in a form of a super elastic plate is inserted into said opening having the rectangular shape.

5. The tool according to claim 1, wherein said tubular member is tapered such that a diameter of the tubular member is gradually changed from about 4 mm at a root to about 2 mm at a tip.

6. The tool according to claim 1, wherein said slit is defined by saw-tooth edges.

7. The tool according to claim 2, wherein said slit is defined by saw-tooth edges.

8. The tool according to claim 3, wherein said slit is defined by saw-tooth edges.

9. The tool according to claim 4, wherein said slit is defined by saw-tooth edges.

10. The tool according to claim 5, wherein said slit is defined by saw-tooth edges.

* * * * *